United States Patent [19]

Stone et al.

[11] Patent Number: 4,958,624
[45] Date of Patent: Sep. 25, 1990

[54] INTERCHANGEABLE LARYNGEAL BLADE

[75] Inventors: R. Douglas Stone, Camillus; Thomas W. Turner, Marcellus, both of N.Y.

[73] Assignee: Welch Allyn, Inc., Skaneateles Falls, N.Y.

[21] Appl. No.: 331,164

[22] Filed: Mar. 31, 1989

[51] Int. Cl.⁵ .............................................. A61B 1/06
[52] U.S. Cl. ...................................................... 128/11
[58] Field of Search ................... 128/10, 11, 303 R, 9, 128/18, 3; 81/489

[56] References Cited

U.S. PATENT DOCUMENTS

| | | | |
|---|---|---|---|
| 3,766,909 | 10/1973 | Ozbey | 128/11 |
| 3,826,248 | 7/1974 | Gobels | 128/11 |
| 4,517,964 | 5/1985 | Upsher | 128/11 |
| 4,570,614 | 2/1986 | Bauman | 128/11 |
| 4,574,784 | 3/1986 | Soloway | 128/11 |
| 4,799,485 | 1/1989 | Furey et al. | 128/11 |

Primary Examiner—Edward M. Coven
Assistant Examiner—Mark S. Graham
Attorney, Agent, or Firm—Wall and Roehrig

[57] ABSTRACT

A laryngeal blade assembly consisting of a metallic blade or spatula and two light assemblies that are selectively mounted on the blade. One light assembly has a fiber optic tube and a base block that with the blade will fit a fiber optic handle. The other light assembly has an incandescent bulb in the end of the light tube and a base block that with the blade fits an incandescent handle.

10 Claims, 2 Drawing Sheets

U.S. Patent    Sep. 25, 1990    Sheet 1 of 2    4,958,624
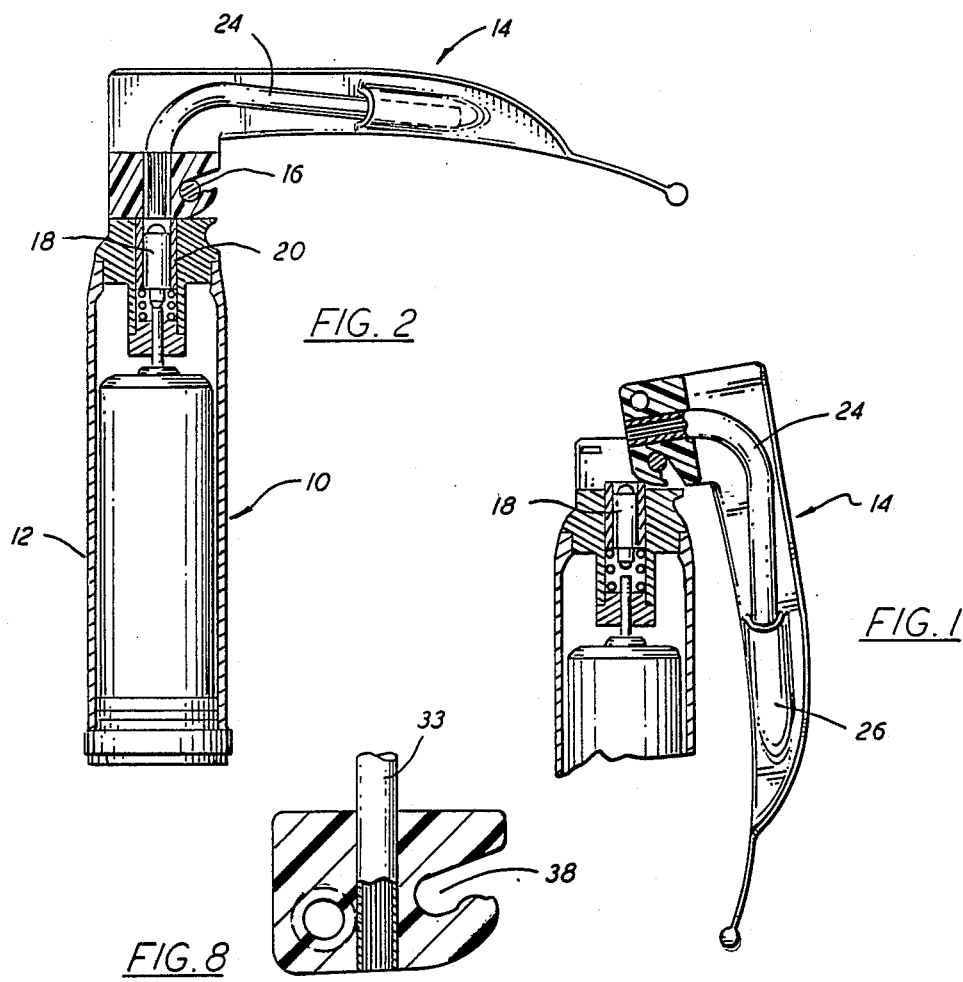
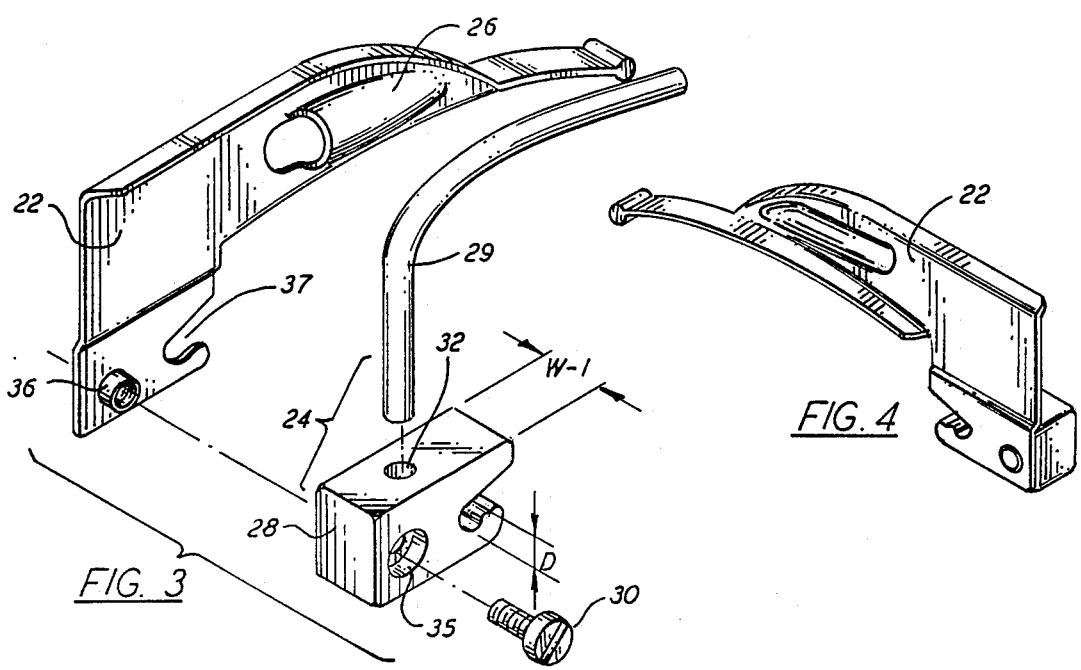

INTERCHANGEABLE LARYNGEAL BLADE

BACKGROUND OF THE INVENTION

This invention relates to laryngoscopes having a handle and a removable laryngeal blade and light assembly. Laryngoscopes are used to examine the larynx; in the introduction and attachment of tracheal tubes in the trachea during intubation narcosis; and other life threatening situations.

Most laryngoscopes consists of a handle portion that contains a power source such as a battery or power cord, a laryngeal blade that will fold flat against the handle and also is completely detachable and a special interlocking mounting for pivotally attaching the laryngeal blade to the handle.

In recent years with the development of fiber optic laryngoscopes in addition to the older incandescent light types it has become important not to accidentally mount the blade of one type on the handle of the other since the construction of the light source of each is sufficiently different that blade assemblies of one type will not operate with handles of another type.

Since as mentioned above situations vital to life are often encountered industry standards have been established by the American Society for Testing and Materials for construction of the different types of laryngoscopes. Basically this standard has required wider bases and larger diameter pivot pins for the fiber optic type blade and handle assemblies than for the conventional incandescent light type blade assemblies. With laryngoscopes made according to this standard it is apparent a fiber optic blade assembly cannot be attached to an incandescent type handle and vice versa.

Prior art showing pivotally mounted blade assemblies includes U.S. Pat. No. 4,273,112 to Heine et al. which is a fiber optic type laryngoscope and U.S. Pat. No. 2,433,705 to H.-L. Palmeter which is a typical incandescent bulb type blade assembly laryngoscope.

OBJECTS AND SUMMARY OF THE INVENTION

According to the present invention there is provided a laryngeal blade assembly consisting of a metallic blade or spatula and two light assemblies that are selectively mounted on the blade. One light assembly has a fiber optic tube and a base block that with the blade will fit a fiber optic handle. The other light assembly has an incandescent bulb in the end of the light tube and a base block that with the blade fits an incandescent handle.

It is therefore an object of the present invention to provide a laryngeal blade that can be used with a plurality of light assemblies.

It is another object of the present invention to provide a laryngeal blade assembly that can selectively be used with fiber optic and incandescent bulb type laryngoscope handles.

It is a further object of the present invention to provide interchangeable fiber optic and incandescent type light assemblies having mounting bases that assembled with a laryngeal blade enable the assembly to mount on a fiber optic and incandescent handle respectively.

It is a still further object of the present invention to provide a laryngeal blade and a plurality of modular light units that selectively can be mounted thereon to form laryngeal blade assemblies capable of fitting a plurality of laryngoscope handles.

It is another object of the present invention to provide a laryngeal blade that can be used with a plurality of different laryngoscopes.

BRIEF DESCRIPTION OF THE DRAWINGS

These and other and further objects of the invention will become apparent from the following description of a preferred embodiment of the invention which is shown in the accompanying drawings with like reference numerals indicating corresponding parts throughout and wherein:

FIG. 1 is a partial cross sectional view of a fiber optic laryngoscope in the folded position;

FIG. 2 is a similar view with the blade assembly in the extended operating position;

FIG. 3 is an exploded perspective view of the fiber optic laryngeal blade assembly of the present invention;

FIG. 4 is a perspective view of the blade of the present invention;

FIG. 8 is a cross sectional view through the base block of FIG. 3.

DESCRIPTION OF THE PREFERRED EMBODIMENT

Figure 5:
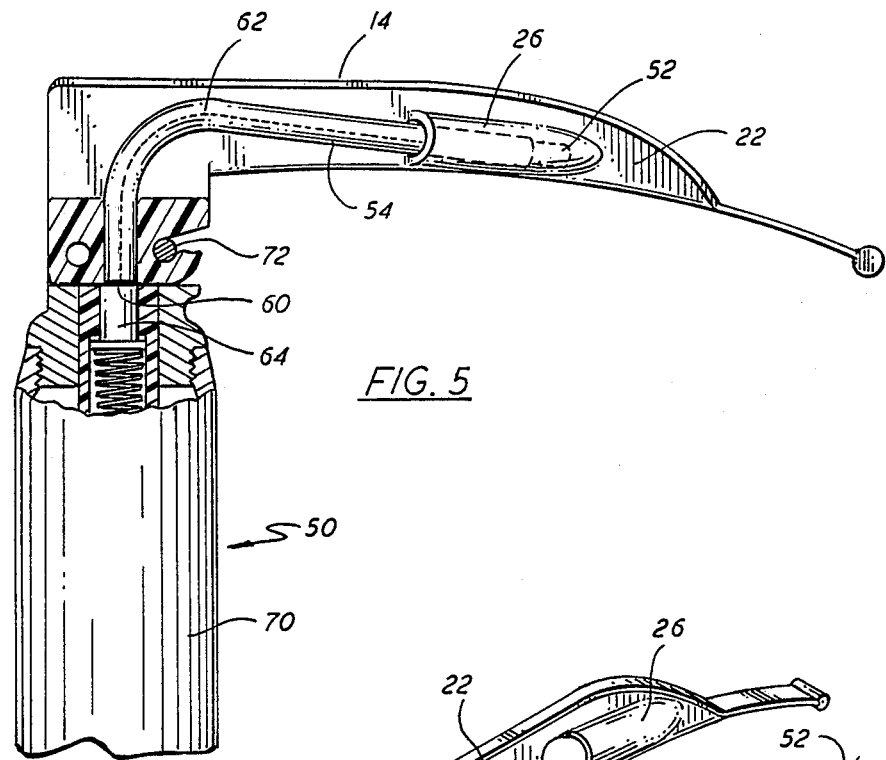
FIG. 5 is a view similar to FIG. 2 of an incandescent lamp laryngoscope according to the present invention.

Referring now to FIGS. 1 and 2 there is shown a laryngoscope 10 having a handle 12, a laryngeal blade assembly 14 mounted on handle 12 about interlocking pin 16 and held in the operative position (FIG. 2) by a latch not shown. Slidably mounted in tube 20 in the head of handle 12 is a light bulb 18, which is de-energized in the folded position of FIG. 1.

Blade assembly 14 (FIG. 3) consists of a metallic blade 22, sometimes called a spatula usually of stainless steel or other easily sterilized metal and a light assembly 24 mounted in a pocket or cavity 26 formed in the wall of the blade 22 and secured to blade 22 by screw 30. Light assembly 24 consists of the tube 29 and block 28 formed into a unitary sub assembly. Tube 29 is bent into a generally right angle shape as shown and is filled with optical fibers to transmit light from bulb 18 to the distal end of tube 29.

Block 28 has a bore 32 to receive one end of the tube 29 and another bore 35 arranged to receive screw 30 which threads into threaded nut 36 which is welded or crimped onto blade 22. Blade 22 at least in the area, matching block 28 is held typically to 0.0615±0.015 inches in thickness. Spatula 22 has a tongue portion and a base portion. A slot 37 is cut in the edge of the base portion to fit over pin 16 and pin 72. Slot 37 in blade 22 is a "universal" slot compared to slots 38 and 66. Block 28 also has a slot 38 cut in one edge. Slot 38 is sized to fit around pin 16 on the cooperative handle 10 and in this embodiment has an effective diameter of 0.185 inches.

Figure 7:
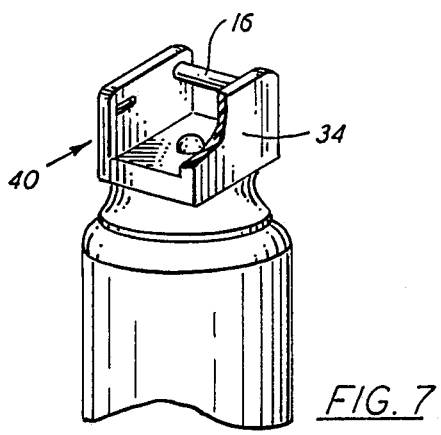
FIG. 7 is a perspective view of the interlocking mount on the handle for a blade assembly.

The width "W" of block 28 is chosen as 0.465 inches such that when mounted on blade 22 the overall combined width will just fit between the walls 34 of a corresponding mounting bracket 40. Shown in FIG. 7 is a bracket 40 that is typical of the type used on laryngoscope handles to receive the laryngeal blade assembly. Bracket 40 will be sized to fit either a fiber optic or incandescent lamp laryngeal blade assembly depending on the handle it is mounted on.

As shown in FIGS. 1. 2 and 7 the sides of bracket 40 are spaced apart in accordance with the above ASTM Standard in this embodiment 0.5280 inches (+0.011–0) to receive the assembly of blade 22 and block 28. Pin 16 is 0.1835" in diameter in this embodiment.

Thus in operation the laryngeal blade assembly 14 will smoothly and snugly fit into its corresponding bracket 40 when raised to the operative position of FIG. 2 and will force bulb 18 into contact with battery contact 19 to illuminate the bulb. Light from bulb 18 is then fed via the optic fibers in tube 29 to the distal end of tube 29 adjacent the end of blade 22 so that it will illuminate the desired target. With blade assembly in the folded position of FIG. 1 light 18 is de-energized.

Figure 6:
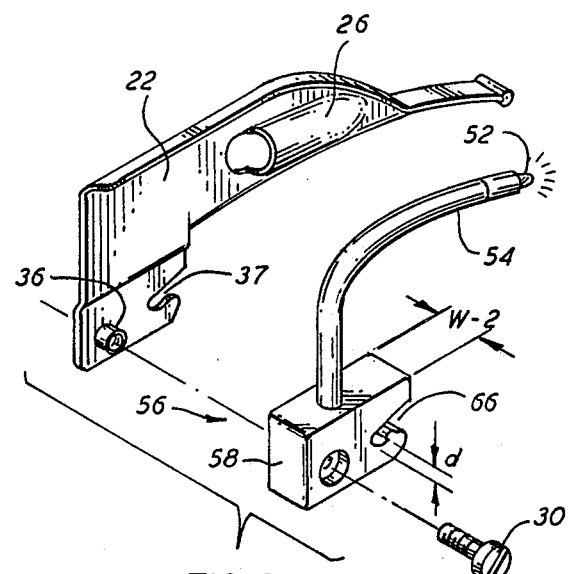
FIG. 6 is a view similar to FIG. 3 of an incandescent bulb blade assembly of the present invention.

Referring now to FIGS. 5–7 there is shown a similar laryngoscope 50 but with a traditional incandescent light bulb 52 mounted in the distal end of a tube 54 which is in turn positioned in cavity 26 on blade 22.

Tube 54 is part of light assembly 56 and is formed in the same approximate right angle configuration as tube 29. Tube 54 terminates in block 58 at flat contact 60. Light bulb 52 is electrically connected by wire 62 within tube 54 to contact 60 for one side of the circuit and blade 22 provides the other side. When blade assembly 14 is in the operative position of FIG. 5 contact 60 engages a contact button 64 which is connected to the battery or other power source not shown and is spring urged into contact therewith.

Base block 58 is similar in configuration to block 28 with similar bores and slots but with different dimensions. In the present embodiment in accordance with the ASTM standards width "W-2" is chosen as 0.439 inches, pin 72 as 0.1615 inches and slot 66 with an effective diameter of 0.163 inches.

Handle 70 FIG. 5 has a mounting bracket similar to bracket 40 with walls spaced apart 0.502+0.11–0 inches to receive block 58 and blade 22 when assembled together. Slot 66 will fit over pin 72 and pivotally secure the blade assembly on handle 70 with a latch mechanism not shown.

The slot 37 in blade 22 as indicated is a universal slot and at least in the incandescent type laryngeal blade assembly offers no interlocking support with the handle. The light assembly base block 58 provides the necessary mutually exclusive interlocking function with the pivot pins of the mating and non mating handles. The combined width of the blade 22 and one of the base blocks 28 or 58 provides the additional mutually exclusive interlocking function with the sides of the mounting bracket on the mating and non mating handles.

Since the cost of blade 22 may run into the hundreds of dollars, it is seen that the present invention provides an economical combination of an easily sterilized and reusable laryngeal blade and interchangeable light assemblies so that a doctor can have available the advantages of each type of light at a significant savings over the cost of two completely separate units. Also the light assemblies 24 and 56 can be made economically enough to be considered disposable units.

Although this invention has been described with reference to one particular embodiment, it should be recognized the invention is not limited to that embodiment. Rather, many modifications and variations would present themselves to those of skill in the art without departing from the scope and spirit of this invention, as defined in the appended claims.

What is claimed is:

1. In a set of non-interchangeable type light laryngoscopes that have a handle and a removable blade-light assembly with mutually exclusive interlocking mounting mechanisms the combination of:
    a first type light sub-assembly comprising a light tube and a first integral base means, said first integral base means adapted to operatively and exclusively engage a first type handle,
    a second type light sub-assembly comprising a light tube and a second integral base means, said second integral base means adapted to operatively and exclusively engage a second type handle,
    a blade having a light sub-assembly engaging member, and
    fastening means for selectively securing said blade to one of said light sub-assemblies,
    such that when said blade is secured to said first type light sub-assembly a first type removable blade-light assembly is provided and when said blade is secured to said second type light sub-assembly a second type removable blade-light assembly is provided.

2. The set of claim 1 wherein the integral base means of the first type light sub-assembly has a greater width than the integral base means of the second type light sub-assembly.

3. The set of claim 1 further defined by the base means of said first and second type light sub-assemblies having cut therein a transverse slot, the slot of said first sub-assembly base means being of a larger effective diameter than the slot of said second light sub-assembly base means.

4. The set of claim 3 wherein said blade has a base portion and a tongue portion, and a slot cut in the base portion thereof said slot having a dimension equal to the slot in the base portion of said first type light sub-assembly.

5. The set of claim 1 further defined by said first and second type light sub-assemblies comprising a bent tube and a base block of integrally molded plastic.

6. In a set of non-interchangeable fiber optic and incandescent type light laryngoscopes that have a handle and removable blade-light assembly with mutually exclusive interlocking mounting mechanisms the combination of:
    a fiber optic type handle adapted to operatively receive a fiber optic light type blade-light assembly,
    an incandescent light type handle adapted to operatively receive an incandescent light type blade-light assembly,
    a fiber optic light sub-assembly comprising a light tube and a first integral base means, said first base means adapted to operatively and exclusively engage a fiber optic type handle,
    an incandescent light sub-assembly comprising a light tube and a second integral base means, said second base means adapted to operatively and exclusively engage an incandescent light type handle,
    a metallic blade having a light sub-assembly engaging member, and
    fastening means for selectively securing said metallic blade to one of said light sub-assemblies,
    so that when said metallic blade is secured to said fiber optic light sub-assembly a fiber optic type removable blade-light assembly is provided which will operatively mount on said fiber optic handle to form a fiber optic laryngoscope and when secured to said incandescent type light sub-assembly an incandescent type removable blade-light assembly is provided which will operatively mount on said incandescent type light handle to form an incandescent light laryngoscope.

7. The set of claim 6 wherein said fiber optic and incandescent type light handles include a mounting bracket comprising a pair of vertical side members and a horizontal pin adapted to interlockingly receive therein said fiber optic and incandescent type light sub-assemblies when they are secured to said blade.

8. The set according to claim 7 wherein the interlocking dimensions of said mounting bracket on said fiber optic handle are greater than the corresponding dimensions on the incandescent light type handle.

9. The set of claim 6 wherein said fiber optic type light sub-assembly includes a plurality of optical fibers in said light tube extending from the base means through said tube.

10. The set of claim 6 wherein said incandescent light sub-assembly includes an incandescent light bulb mounted in one end of said light tube, a contact button in the base means, and an electrical conductor electrically connecting said bulb to said contact button.

* * * * *